US006610277B2

(12) United States Patent
Zuckerman

(10) Patent No.: US 6,610,277 B2
(45) Date of Patent: Aug. 26, 2003

(54) APPETITE SUPPRESSANT TOOTHPASTE

(76) Inventor: Arthur Zuckerman, 614 Second Ave., New York, NY (US) 10016

(*) Notice: Subject to any disclaimer, the term of this patent is extended or adjusted under 35 U.S.C. 154(b) by 0 days.

(21) Appl. No.: 10/302,109

(22) Filed: Nov. 22, 2002

(65) Prior Publication Data

US 2003/0077233 A1 Apr. 24, 2003

Related U.S. Application Data

(63) Continuation of application No. 09/749,021, filed on Dec. 27, 2000, now Pat. No. 6,485,710.

(51) Int. Cl.$^7$ ............................. A61K 7/26; A61K 35/78
(52) U.S. Cl. ...................... 424/58; 424/49; 424/195.1; 424/725
(58) Field of Search ..................... 424/49–58

(56) References Cited

U.S. PATENT DOCUMENTS

| | | | | |
|---|---|---|---|---|
| 5,470,565 A | * | 11/1995 | Hayakawa et al. ............ 424/52 |
| 5,472,684 A | * | 12/1995 | Nabi et al. ..................... 424/49 |
| 5,612,039 A | * | 3/1997 | Policappelli et al. .... 424/195.1 |
| 5,626,849 A | * | 5/1997 | Hastings et al. .......... 424/195.1 |
| 5,911,992 A | * | 6/1999 | Braswell et al. ......... 424/195.1 |
| 5,945,107 A | * | 8/1999 | Hessel et al. ............. 424/195.1 |
| 6,025,363 A | * | 2/2000 | Giles .......................... 514/263 |
| 6,080,401 A | * | 6/2000 | Reddy et al. ............. 424/195.1 |
| 6,113,949 A | * | 9/2000 | Brink ......................... 424/602 |
| 6,277,396 B1 | * | 8/2001 | Dente ......................... 424/439 |
| 6,316,499 B1 | * | 11/2001 | Jones ......................... 514/534 |
| 6,319,523 B1 | * | 11/2001 | Zhou .......................... 424/725 |
| 6,322,838 B1 | * | 11/2001 | Guntert et al. ................ 424/49 |
| 6,485,710 B2 | * | 11/2002 | Zuckerman ................... 424/58 |
| 2002/0122777 A1 | * | 9/2002 | Zuckerman ................... 424/58 |

FOREIGN PATENT DOCUMENTS

| | | | |
|---|---|---|---|
| EP | 515755 | * | 12/1992 |
| EP | 1010429 | * | 6/2000 |
| WO | 97/30601 | * | 8/1997 |
| WO | 98/02165 | * | 1/1998 |
| WO | 99/43293 | * | 9/1999 |
| WO | 00/15051 | * | 3/2000 |
| WO | 00/41708 | * | 7/2000 |
| WO | 01/19158 | * | 3/2001 |

OTHER PUBLICATIONS

Google's Abstract Botanical.com.*
Green Tea Toothpaste, Apr. 18, 2001.*
Myrra Toothpowder Mouthwash, Apr. 18, 2001.*
Guggul Obesity, Apr. 18, 2001.*
Black Current Seed Oil, Apr. 18, 2001.*
Garcinia Cambogia Guarawa, Apr. 18, 2001.*
Gymnema Syvestre Griffonia Simplicifolia, Apr. 18, 2001.*
Kola Nut Bitter Orange Peel Yerbe Mate, Apr. 18, 2001.*

* cited by examiner

*Primary Examiner*—Shep K. Rose
(74) *Attorney, Agent, or Firm*—Ezra Sutton

(57) ABSTRACT

An appetite suppressant toothpaste formulations which simultaneously suppresses the users appetite while promoting intraoral cleanliness. The toothpaste composition includes toothpaste base ingredients; and at least one of appetite suppressant and appetite depressant herbs. The toothpaste base ingredients include a combination of known amounts of Vegetable Glycerin; Sorbitol, Hydrated Silica; Purified Water; Xylitol; Carrageenan; Sodium Lauryl Sulfate; and Titanium Dioxide and a flavoring agent. The appetite suppressing and depressing herbs include at least one of Garcinia Cambogia; Gymnema Sylvestre; Kola Nut; Citrus Aurantium; Yerba Mate; and Griffonia Simplicifolia and comprise a range of substantially 5.5% to substantially 22% by weight of the composition. The appetite suppressing and depressing herbs may further include at least one of Guarana, Green Tea, myrrh, guggul Lipid and black current seed oil. Alternatively, the toothpaste composition may be in the form of a dental cream or mouthspray.

13 Claims, No Drawings

APPETITE SUPPRESSANT TOOTHPASTE

RELATED APPLICATION

This is a continuation application of U.S. patent application Ser. No. 09/749,021, filed on Dec. 27, 2000 and published Sep. 5, 2002. U.S. 2002/01 22777A1; now U.S. Pat. No. 6,485,710 B2, dated Nov. 26, 2002.

BACKGROUND OF THE INVENTION

1. Field of the Invention

The present invention relates to toothpaste and, more particularly, to a formulation of an appetite suppressant oral composition in the form of a toothpaste comprising ingredients which co-act to control the appetite and permit reduction in body weight by brushing the teeth of a user with the composition.

It has been found that the combination of about 5.50–22.0% by weight natural herbs functions as an appetite suppressant agent in a standard toothpaste formulation. This unexpected result from the novel toothpaste composition of the present invention to suppress appetite and promote weight loss provides a new secondary benefit to the promoting intraoral cleanliness with toothpaste.

2. Description of the Prior Art

Numerous types of appetite suppressants have been provided in the prior art. Current products to suppress appetite and control weight are generally drugs with undesirable side effects, often with a propensity to be addictive; whereas the instant novel appetite suppressant toothpaste provides a non-pharmacological means to suppress the appetite of a user by adding natural herbs to a standard toothpaste formulation.

There are many appetite suppressant products on the market, both prescription items and over the counter products. Most of these products act as central nervous system stimulants, such as amphetamines, or have a similar mechanism of action. Many of the over the counter products, such as Acutrim, Dexatrim, Appedrine, etc. contain Phenylpropanolamine HCl+Caffeine. Ayds, another well known appetite suppressant product, is a caramel candy containing Benzocaine.

Oral compositions which contain natural herbs for temporary relief of pain in the oral cavity are well known products. Such products are readily found on the market and include Anbesol gel, a liquid comprising phenol, alcohol and Benzocaine; Chloroseptic losengers containing menthol-benzocaine, corn syrup, glycerine, sucrose and flavor for temporary relief of sore throat pain; and Hurricane Topical anesthetic aerosol spray for controlling oral pain.

For example, U.S. Pat. Nos. 3,856,942 and 4,913,894 are illustrative of such prior art. However, none of the above cited prior art disclose an appetite suppressant toothpaste formulation for controlling weight, comprising a suppressing agent containing natural herbs. These prior art references also do not provide an appetite suppressant in a dental vehicle which may be in the form of a toothpaste, dental cream or mouth spray. The concept of a toothpaste formulation containing an appetite suppressing agent is novel. While these units may be suitable for the particular purpose to which they address, they would not be as suitable for the purposes of the present invention as heretofore described.

This patent discloses an appetite control composition which is readily ingested, comprising a candy base of sucrose and maltose, caffeine, Natural herbs, vitamins and optionally flavors including quinine to reduce the sweetness of the sucrose and maltose. This composition is preferably a slow-dissolving hard candy or tablet, but may also be in the form of gum drops, chocolate bars or drops, cotton candy, lozenges or gelatin desserts, all of which are ingestible.

This patent discloses an appetite suppressant oral composition containing benzocaine, high impact flavor and a sweetening agent, in the form of a toothpaste. A novel method of reducing appetite and thereby intended for controlling weight of consumers, which comprises applying to the oral cavity a high impact flavor in a toothpaste.

SUMMARY OF THE PRESENT INVENTION

The present invention relates to toothpaste and, more particularly, to a formulation of an appetite suppressant oral composition in the form of a toothpaste comprising ingredients which co-act to control the appetite and permit reduction in body weight by brushing the teeth of a user with the composition.

A primary object of the present invention is to provide an appetite suppressant toothpaste that will overcome the shortcomings of prior art devices.

The present invention provides an appetite suppressant toothpaste intended to effect weight control. The toothpaste is formulated by adding an appetite suppressing agent comprising about 5.50–22.00% by weight natural herbs to a standard dentifrice or toothpaste. Appetite suppression and weight control can be obtained by brushing the teeth, before and/or after each meal, preferably before, on a regular basis such as three times/day with the appetite suppressant toothpaste of the present invention.

Accordingly, another object of present invention is to provide an appetite suppressant toothpaste formulation by the incorporation of an appetite suppressant agent comprising natural herbs.

A further object of the present invention is to provide an appetite suppressant toothpaste which is able to reduce the appetite of a user alter brushing the teeth of the user with the toothpaste A yet further object of this invention is to provide an appetite suppressant toothpaste in the form of a dental cream or mouthspray for use preferably prior to meals, to promote weight loss.

Still another object of present invention is to provide an appetite suppressant toothpaste for promoting weight loss as well as good dental hygiene.

Another object of present invention is to provide an appetite suppressant toothpaste formed from a novel essentially non-ingested composition containing safe natural herbs able to suppress the appetite and promote weight loss of the user.

Another object of the present invention is to provide an appetite suppressant toothpaste that is simple and easy to use.

A still further object of the present invention is to provide an appetite suppressant toothpaste that is economical in cost to manufacture Additional objects, advantages and novel features of the invention will be set forth in part in the description which follows, and in part will become apparent to those skilled in the art upon examination of the following or may be learned by practice of the invention.

Additional objects of the present invention will appear as the description proceeds.

An appetite suppressant toothpaste formulations which simultaneously suppresses the users appetite while promoting intraoral cleanliness is disclosed by the present invention. The toothpaste composition includes toothpaste base ingredients; and at least one of appetite suppressant and appetite depressant herbs. The toothpaste base ingredients include a combination of known amounts of Vegetable Glycerin; Sorbitol, Hydrated Silica; Purified Water; Xylitol; Carrageenan; Sodium Lauryl Sulfate; and Titanium Dioxide and a flavoring agent. The appetite suppressing and depressing herbs include at least one of Garcinia Cambogia; Gymnema Sylvestre; Kola Nut; Citrus Aurantium; Yerba Mate; and Griffonia Simplicifolia and comprise a range of substantially 5.5% to substantially 22% by weight of the composition. The appetite suppressing and depressing herbs may further include at least one of Guarana, Green Tea, myrrh, guggul Lipid and black current seed oil. Alternatively, the toothpaste composition may be in the form of a dental cream or mouthspray.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

DETAILED DESCRIPTION OF THE PREFERRED EMBODIMENT

To achieve the foregoing and other objects in accordance with the present invention, as embodied and broadly described herein, the appetite suppressant toothpaste comprises about 5.50–22.0% by weight natural herbs. The amount of natural herbs effective in minimizing the desire for food and suppress appetite of a user is about 5.50 to 22.00 wt %.

Another component in the appetite suppressant toothpaste composition is a high impact flavor which is an intense flavor including, but not limited to, any or all of oil of wintergreen, chocolate, cherry, strawberry, grape and other hunger minimizing flavors. The high impact flavor is a blend of a number of components so that the resultant mixture is a well-rounded, smooth flavor with an intense immediate initial impact, a lasting pleasant aftertaste (e.g. preferably at least about 45–60 seconds) and a prolonged pleasantly smelling impact on the breath of the user. Other food grade artificial flavors may be used provided they are intense flavors of high initial impact with a lasting pleasant aftertaste.

The standard toothpaste base of the instant invention preferably comprises substantially from 10–30% Vegetable Glycerin; substantially from 10–30% Sorbitol; substantially from 10–30% Hydrated Silica; substantially from 10–30% Purified Water; substantially from 10–30% Xylitol; substantially from 1–3% Carrageenan; substantially from 1–3% Sodium Lauryl Sulfate; substantially from 1–3% Titanium Dioxide; and substantially from 0.30–1% Oil of Wintergreen. Sorbitol is the major humectant ingredient because of its sweet taste. Minimal amounts of polyethylene are used due to its bitter taste. A mixture of sorbitol and glycerin is preferred. In the toothpaste, dental gel or dental cream, the humectant constitutes about 65–75% by weight of the composition and the water content is about 10–30% by weight of the toothpaste.

It is preferred to use a gelling agent in dental creams or gels, such as the natural and synthetic gums and gum like materials, for example Carrageenan, Irish moss, gum tragacanth, cellulose gums such as methyl cellulose, carboxymethyl cellulose, hydroxyethyl cellulose, hydroxmethyl cellulose, polyvinylpyrrolidone, hydrophilic colloidal carboxyvinyl polymers, such as those sold under the trademark Carbopol 934 and 940 and synthetic silicated clays such as those sold under the trademark Laponite CP and Laponite SP. These grades of Laponite have the formula $(Si_8 Mg_5 Li_{0.6} O_{24})^{0.6-} – Na^{0.6+}$. The gelling agent constitutes about 1.0–3.0% by weight of the toothpaste formulation.

The toothpaste formulations will generally also include a dentally acceptable, substantially water insoluble polishing agent of the type commonly employed in dental creams. Representative polishing agents include, for example, dicalcium phosphate, tricalcium phosphate, insoluble sodium metaphosphate, aluminum hydroxide, including hydrated alumina, colloidal silica, hydrated silica, precipitated silica and magnesium carbonate, calcium carbonate, calcium pyrophosphate, and bentonite, including suitable mixtures thereof. It is preferred to use silica-containing polishing agents such as amorphous hydrated silicon dioxide $(SiO_2H_2O)$, known as Zeodent/Zeofree/Zeosyl/Zeothix obtainable from J.M. Huber Corporation, which is in the form of a white, odorless powder having an average particle size of 8–10 micrometers and a density of 2 g/ml. at 25° C. Amorphous silica, also called silica gel and silicic acid, is also obtainable from W.R. Grace & Co. as Sylodent 704 which is a dry white powder having an average particle size of 4 microns and a specific gravity of 2.1. Sylox® is another amorphous silica provided by W.R. Grace & Co., in the form of a dry white powder having an average size of 1.5–12 microns. The preferred siliceous containing polishing agent constitutes about 10–30% by weight of the dental cream formulations.

When the toothpaste is a visually clear gel or opacified gel, a polishing agent of colloidal silica, such as those sold under the trademark Syloid as Syloid 72 and Syloid 74 or under the trademark Santocel as Santocel 100 and synthetic alkali metal aluminosilicate complexes (including silica containing combined alumina) may be particularly useful. They have refractive indices close to the refractive indices of gelling agents-liquid systems commonly used in toothpaste (which generally include humectants such as glycerine and sorbitol).

Organic surface-active agents are preferably used in the composition of the present invention to assist in achieving thorough and complete dispersion of the compositions of the present invention throughout the oral cavity and render the said compositions more cosmetically acceptable. The organic surface-active agent material may be anionic or nonionic, in nature, and it is preferred to employ as the surface-active agent a detersive material which imparts to the composition detersive and foaming properties. Suitable anionic surfactants include water-soluble salts of higher fatty acid monoglyceride monosulfates, such as the sodium salt of the monosulfated monoglyceride of hydrogenated coconut oil fatty acids, higher alkyl sulfates, such as sodium lauryl sulfate, alkyl aryl sulfonates, such as sodium dodecyl benzene sulfonate, higher alkyl sulfoacetates, higher fatty acid esters of 1,2-dihydroxy propane sulfonates, olefin sulfonates and the like.

Other particularly suitable surface active materials include nonionic agents such as condensates of sorbitan monostearate with approximately 20 moles of ethylene oxide; condensates of ethylene oxide with propylene oxide; condensates of propylene glycol (Pluronics); condensation products of an alpha-olefin oxide containing 10 to 20 carbon atoms; a polyhydric alcohol containing 2 to 10 carbons; and 2 to 6 hydroxyl groups and either ethylene oxide or a heteric mixture of ethylene oxide and propylene oxide. The resultant detergents are heteric polymers having a molecular weight in the range of 400 to 1600 and containing 40% to 80% by weight of ethylene oxide, with an alpha-olefin oxide to polyhydric alcohol mole ratio in the range of 1:1 to 1:3. The amount of anionic or nonionic surfacant constitutes about 1–3% by weight of the toothpaste formulation.

The toothpaste of this invention may also contain conventional additional ingredients such as coloring or whitening agents and preservatives. These additional ingredients may each be added to the toothpaste in minimal amounts of up to 5% by weight, and preferably up to 1%, provided they do not interfere with the appetite suppressant and compatibility properties of the finished product.

The toothpaste of this invention is prepared by conventional methods of making toothpaste and/or dental creams or dental gels. More specifically, the gelling agent such as a cellulose gum is dispersed in glycerine, to which is added an aqueous solution containing the sweetening agent such as xylitol, followed by the addition of sorbitol and mixing for a period of about 20 minutes to hydrate the gum, mixing the gum mixture with the polishing agent in a mixer under a vacuum of 28–30 inches of pressure. Lastly, the flavor, the surfactant and natural herbs are added to the vacuum mixer, mixed for a period of about 15 minutes, and the final mixture is placed in a tube. In the practice of this invention to suppress appetite, control weight and simultaneously promote oral hygiene, the toothpaste according to this invention is applied regularly to the oral cavity by brushing the teeth or spraying the mouth for 30–90 seconds, at least three times a day either after or before meals, preferably prior to eating meals.

The toothpaste composition of the present invention has a molecule size which is small enough to be absorbed through the mucous membrane of the mouth. The composition is also water soluble, and is absorbed into the person's blood stream to act as an appetite suppressant.

The following embodiments are further illustrative of the nature of the present invention, but it is understood that the invention is not limited thereto. The compositions are prepared in the usual manner and all amounts and proportions referred to herein and in the appended claims are by weight unless otherwise indicated.

The preferred embodiment of the appetite suppressant toothpaste is:

EMBODIMENT 1
APPETITE SUPPRESSANT TOOTHPASTE

| INGREDIENTS | | Percent % | |
|---|---|---|---|
| Vegetable Glycerin | | 10.00–30.00 | |
| Sorbitol | | 10.00–30.00 | (Basic |
| Hydrated Silica | | 10.00–30.00 | Toothpaste |
| Purified Water | | 10.00–30.00 | Base) |
| Xylitol | | 10.00–30.00 | |
| Carraqeenan | | 1.00–3.00 | |
| Sodium Lauryl Sulfate | | 1.00–3.00 | |
| Titanium Dioxide | | 1.00–3.00 | |
| Oil of Wintergreen | | 0.30–1.00 | |
| Garcinia cambogia | | 1.00–2.00 | |
| Gymnema Sylvestre | (All have | 1.00–2.00 | |
| Kola Nut | common | 1.00–2.00 | |
| Citrus Aurantium | function &/or | 1.00–2.00 | |
| Yerba Mate | compliment | 1.00–2.00 | |
| Griffonia Simplicifolia | each other) | 0.40–2.00 | |

Further embodiments of the appetite suppressant toothpaste according to the present invention are as follows:

APPETITE SUPRESSANT TOOTHPASTE

| INGREDIENTS | | Percent % | |
|---|---|---|---|
| EMBODIMENT 2 | | | |
| Vegetable Glycerin | | 10.00–30.00 | |
| Sorbitol | | 10.00–30.00 | (Basic |
| Hydrated Silica | | 10.00–30.00 | Toothpaste |
| Purified Water | | 10.00–30.00 | Base) |
| Xylitol | | 10.00–30.00 | |
| Carraqeenan | | 1.00–3.00 | |
| Sodium Lauryl Sulfate | | 1.00–3.00 | |
| Titanium Dioxide | | 1.00–3.00 | |
| Oil of Wintergreen | | 0.30–1.00 | |
| Garcinia cambogia | | 1.00–2.00 | |
| Gymnema Sylvestre | (All have | 1.00–2.00 | |
| Kola Nut | common | 1.00–2.00 | |
| Citrus Aurantium | function &/or | 1.00–2.00 | |
| Yerba Mate | compliment | 1.00–2.00 | |
| Griffonia Simplicifolia | each other) | 0.40–2.00 | |
| Guarana | | 1.00–2.00 | |
| Green Tea | | 1.00–2.00 | |
| EMBODIMENT 3 | | | |
| Vegetable Glycerin | | 10.00–30.00 | |
| Sorbitol | | 10.00–30.00 | (Basic |
| Hydrated Silica | | 10.00–30.00 | Toothpaste |
| Purified Water | | 10.00–30.00 | Base) |
| Xylitol | | 10.00–30.00 | |
| Carraqeenan | | 1.00–3.00 | |
| Sodium Lauryl Sulfate | | 1.00–3.00 | |
| Titanium Dioxide | | 1.00–3.00 | |
| Oil of Wintergreen | | 0.30–1.00 | |
| Garcinia cambogia | | 1.00–2.00 | |
| Gymnema Sylvestre | (All have | 1.00–2.00 | |
| Kola Nut | common | 1.00–2.00 | |
| Citrus Aurantium | function &/or | 1.00–2.00 | |
| Yerba Mate | compliment | 1.00–2.00 | |
| Griffonia Simplicifolia | each other) | 0.40–2.00 | |
| Myrrh | | 1.00–2.00 | |
| EMBODIMENT 4 | | | |
| Vegetable Glycerin | | 10.00–30.00 | |
| Sorbitol | | 10.00–30.00 | (Basic |
| Hydrated Silica | | 10.00–30.00 | Toothpaste |
| Purified Water | | 10.00–30.00 | Base) |
| Xylitol | | 10.00–30.00 | |
| Carraqeenan | | 1.00–3.00 | |
| Sodium Lauryl Sulfate | | 1.00–3.00 | |
| Titanium Dioxide | | 1.00–3.00 | |
| Oil of Wintergreen | | 0.30–1.00 | |
| Garcinia cambogia | | 1.00–2.00 | |
| Gymnema Sylvestre | (All have | 1.00–2.00 | |
| Kola Nut | common | 1.00–2.00 | |
| Citrus Aurantium | function &/or | 1.00–2.00 | |
| Yerba Mate | compliment | 1.00–2.00 | |
| Griffonia Simplicifolia | each other) | 0.40–2.00 | |
| Guarana | | 1.00–2.00 | |
| Green Tea | | 1.00–2.00 | |
| Myrrh | | 1.00–2.00 | |
| EMBODIMENT 5 | | | |
| Vegetable Glycerin | | 10.00–30.00 | |
| Sorbitol | | 10.00–30.00 | (Basic |
| Hydrated Silica | | 10.00–30.00 | Toothpaste |
| Purified Water | | 10.00–30.00 | Base) |
| Xylitol | | 10.00–30.00 | |
| Carraqeenan | | 1.00–3.00 | |
| Sodium Lauryl Sulfate | | 1.00–3.00 | |
| Titanium Dioxide | | 1.00–3.00 | |
| Oil of Wintergreen | | 0.30–1.00 | |
| Garcinia cambogia | | 1.00–2.00 | |
| Gymnema Sylvestre | (All have | 1.00–2.00 | |
| Kola Nut | common | 1.00–2.00 | |
| Citrus Aurantium | function &/or | 1.00–2.00 | |

-continued

APPETITE SUPRESSANT TOOTHPASTE

| INGREDIENTS | | Percent % | |
|---|---|---|---|
| Yerba Mate | compliment | 1.00–2.00 | |
| Griffonia Simplicifolia | each other) | 0.40–2.00 | |
| Guarana | | 1.00–2.00 | |
| Green Tea | | 1.00–2.00 | |
| Myrrh | | | 1.00–2.00 |
| Guggul | | 1.00–2.00 | |
| Black current seed oil | | 1.00–2.00 | |
| EMBODIMENT 6 | | | |
| Vegetable Glycerin | | 10.00–30.00 | |
| Sorbitol | | 10.00–30.00 | (Basic) |
| Hydrated Silica | | 10.00–30.00 | Toothpaste |
| Purified Water | | 10.00–30.00 | Base) |
| Xylitol | | 10.00–30.00 | |
| Carraqeenan | | 1.00–3.00 | |
| Sodium Lauryl Sulfate | | 1.00–3.00 | |
| Titanium Dioxide | | 1.00–3.00 | |
| Oil of Wintergreen | | 0.30–1.00 | |
| Garcinia cambogia | | 1.00–2.00 | |
| Gymnema Sylvestre | (All have | 1.00–2.00 | |
| Kola Nut | common | 1.00–2.00 | |
| Citrus Aurantium | function &/or | 1.00–2.00 | |
| Yerba Mate | compliment | 1.00–2.00 | |
| Griffonia Simplicifolia | each other) | 0.40–2.00 | |
| Guarana | | 1.00–2.00 | |
| Green Tea | | 1.00–2.00 | |
| Guggul | | 1.00–2.00 | |
| Black current seed oil | | 1.00–2.00 | |
| Myrrh | | 1.00–2.00 | |

The toothpaste compositions illustrated above have intense flavor and suppress the appetite of the consumer after brushing their teeth therewith. This provides a harmless topical means of controlling weight without ingesting drugs, troches, lozenges, gums, or the like.

Variations in the above formulations may be made. For example, other food grade anionic or nonionic surfactants may be substituted for the sodium lauryl sulfate or polyoxyethylene sorbitan diiostearate surfactants. Similarly, other dental polishing agents may be substituted for tile specific silica polishing agent in the specific examples. Likewise, other high impact or intense flavoring composition may be used in lieu of the oil of wintergreen or cheesecake flavors, such as chocolate, mint, strawberry, grape or the like.

Since the invention is described with reference to a couple of preferred embodiments, and since numerous additional modifications and changes may become readily apparent to those skilled in the art after reading this disclosure, it should be understood that I do not wish to limit the scope of my invention to the exact composition described above, and claimed by me below.

From the above description it can be seen that the appetite suppressant toothpaste of the present invention is able to overcome the shortcomings of prior art devices by providing an appetite suppressant toothpaste by the incorporation of an appetite suppressant agent comprising natural herbs. The appetite suppressant toothpaste in preferably in the form of a dental cream and mouthspray for use preferably prior to meals, to promote weight loss as a new secondary benefit to a toothpaste. The appetite suppressant toothpaste promotes weight loss via a toothpaste formulation containing safe natural herbs. Furthermore, the appetite suppressant toothpaste of the present invention is simple and easy to use and economical in cost to manufacture.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. A toothpaste, dental cream, or mouth spray composition which suppresses appetite and promotes weight loss while simultaneously promoting intraoral cleanliness, comprising:
   a) toothpaste, dental cream, or mouth spray base ingredients; and
   b) a combination of appetite suppressants comprising effective amounts of Griffonia Simplicifolia, Gymnema Sylvestre, and Citrus Aurantium, being present at about 5.5% to about 22% by weight concentrations.

2. A toothpaste composition in accordance with claim 1, further including Garcinia Cambogia.

3. A toothpaste composition in accordance with claim 2, further including Guarana.

4. A toothpaste composition in accordance with claim 3, further including Yerba Mate.

5. A toothpaste composition in accordance with claim 4, further including Kola Nut.

6. A toothpaste composition in accordance with claim 5, further including Green Tea and Myrrh gum.

7. A toothpaste composition in accordance with claim 6, wherein each of said further appetite suppressants comprises substantially 1% to 2% by weight of said composition.

8. A toothpaste composition in accordance with claim 1, being in the form of a dental cream.

9. A toothpaste composition in accordance with claim 1, being in the form of a mouth spray.

10. A toothpaste composition which suppresses appetite and promotes weight loss while simultaneously promoting intraoral cleanliness, comprising:
    a) toothpaste base ingredients; and
    b) a combination of appetite suppressants comprising effective amounts of Garcinia Cambogia, Gymnema Sylvestre, and Kola Nut, being present at about 5.5% to about 22% by weight concentrations.

11. A toothpaste composition which suppresses appetite and promotes weight loss simultaneously promoting intraoral cleanliness, comprising:
    a) toothpaste base ingredients; and
    b) a combination of appetite suppressants comprising effective amounts of Garcinia Cambogia, Kola Nut, and Citrus Aurantium, being present at about 5.5% to about 22% by weight concentrations.

12. A toothpaste composition in accordance with claim 11, further including Yerba Mate.

13. A toothpaste composition in accordance with claim 12, further including Griffonia Simplicifolia.

* * * * *